United States Patent [19]
Wilson et al.

[11] Patent Number: 5,249,137
[45] Date of Patent: Sep. 28, 1993

[54] COMPUTER-AIDED CHEMICAL ILLUSTRATION SYSTEM

[75] Inventors: James S. Wilson, Long Beach; William R. Mallgren; Janaia M. Donaldson, both of Portola Valley, all of Calif.; Samuel Kaplan, Walworth; John S. Facci, Webster, both of N.Y.

[73] Assignee: Xerox Corporation, Stamford, Conn.

[21] Appl. No.: 498,566

[22] Filed: Mar. 23, 1990

[51] Int. Cl.⁵ .............................................. G06F 15/20
[52] U.S. Cl. ..................................... 364/496; 395/147
[58] Field of Search ................ 364/496, 578, 419, 497, 364/499, 523; 434/278, 279, 280, 281, 283; 436/8, 182, 183; 395/145, 147, 148

[56] References Cited

U.S. PATENT DOCUMENTS

| | | | |
|---|---|---|---|
| 4,810,197 | 3/1989 | Hicks | 434/278 |
| 4,835,528 | 5/1989 | Flinchbaugh | 340/709 |
| 4,855,931 | 8/1989 | Sounders et al. | 434/278 |
| 4,980,840 | 12/1990 | Yin et al. | 364/523 |

OTHER PUBLICATIONS

Sutherland, Sketchpad: A Man-Machine Graphical Communication System, Conf. Proc. Spring Joint Computer Conf. (1963).
Bier, Snap–Dragging, Siggraph 86 Proceedings, vol. 20, No. 4 Aug. 18–22, 1986, pp. 233–240.
Neuman, Principles of Interactive Computer Graphics, McGraw–Hill, 1979.
Rubenstein; "Chemdraw"; 1985 (version 2.0).
Chiwiter; PC Magazine Advertisement Jul. 1988.
Chemical Version 3.1 Overview 1987, 1988.
Chemical Commands Oct. 28, 1988.
Chemical Version 3.1 program (floppy disk) Oct. 28, 1988.

*Primary Examiner*—Jack B. Harvey
*Assistant Examiner*—Ellis B. Ramirez
*Attorney, Agent, or Firm*—Townsend and Townsend Khourie and Crew

[57] ABSTRACT

A computer-aided chemical illustration system is disclosed. Techniques provided include: 1) efficient drawing of bonds; 2) drawing different bond types during a single mode; 3) determining bisect angles for bonds; 4) labeling atoms on the fly; 5) automatic alignment of atom labels; 6) custom alignment of atom labels; 7) changing the type, style, or orientation of an object while it is being drawn; 8) detection of ring structures; and 9) shifting bonds around on a ring.

44 Claims, 19 Drawing Sheets

———COOH

COMPUTER-AIDED CHEMICAL ILLUSTRATION SYSTEM

BACKGROUND OF THE INVENTION

This invention relates generally to computer-aided chemical illustration systems. Specifically, it relates to a system for emulating the illustration tools used in making precise drawings of chemical structures.

The accurate representation of molecules remains a problem for scientists. The use of molecular formulas represents an early attempt at describing molecules. For example, dibromo-ethane can be represented by the molecular formula $C_2H_4Br_2$. However, molecular formulas do not necessarily indicate molecular structure—an aspect which is crucial to the communication of chemical structures.

In particular, molecular formulas do not readily illustrate the variation between isomers, i.e., where two structurally different compounds have the same molecular formula. Even chemical names, which distinguish between isomers, may be difficult to interpret for more complex molecules. For example, carbenicillin, a common antibiotic, has an empirical molecular formula of $C_{26}H_{25}N_2NaO_6S$. Its chemical name is 1-(5-Indanyl)-N-(2-carboxy-3, 3-dimethyl-7-oxo-4-thia-I-azabicyclo[3.2.0] hept-6-yl)-2-phenyl-malonate. However, most readers would not be able to discern carbenicillin's structure from this information. Clearly, a better method is desired to indicate chemical structures.

Structural formulas, first developed by Crum Brown in 1864, attempt to depict three-dimensional molecular structures with two-dimensional drawings. The development and use of structural formulas is well known in the art (see Roberts, J. and Caserio, M., Basic Principles of Organic Chemistry, W. A. Benjamin, Inc., 1977).

For the most part, structural formulas emphasize ease of drawing over geometric accuracy. Three-dimensional detail is commonly omitted. It is understood that the technical reader will infer the three-dimensional structure from the two-dimensional structural formula.

Methane ($CH_4$) illustrates this point. It is well established that the carbon atom in methane forms its four single bonds at the corners of a regular tetrahedron, i.e., bond angles equal to 109.5°. However, it is much easier to draw this as a planar structure. Therefore, methane is represented as a cross-shaped molecule with a carbon (C) atom in the center of four evenly-spaced hydrogen (H) atoms:

While methane appears to be a flat molecule with bond angles of 90, the technical reader will infer a tetrahedron. Alternatively, one may draw a more detailed or "projection" structural formula to emphasize methane's tetrahedral nature:

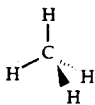

Both structural formulas represent two-dimensional depictions of a three-dimensional molecule.

Arguably, a molecule is more accurately represented by three-dimensional models, such as ball and stick or space-filling models. Additional illustration techniques, such as shading or perspective geometry, could be added to structural formulas to yield more accurate renditions. However, these are more difficult and time consuming to create and add little information to the informed scientific reader. The structural formula method is a good compromise between ease of use and geometric accuracy. As a result, it retains great popularity with scientists and technical writers.

While scientists and technical writers have traditionally relied upon templates and pencils to create structural formulas, the human hand can rarely, if ever, achieve the precision that is available with computer-aided systems. As a result, computers have become a powerful tool for the rapid and economical creation of pictures. The use of computer graphics is particularly well suited for automating chemical illustrations.

In computer-aided chemical illustration systems, each object (ring, atom, bond, chemical formula, etc.) exists as an independent constituent with its own attributes. For example, instead of creating a chemical bond by drawing continuously, as one would do by hand, the user need only specify the beginning and ending points. The computer generates a line representing the bond specified by these points. Once an object is entered into the computer, the user may perform various operations which would be difficult or impossible to do manually.

However, current systems have several drawbacks. For example, prior systems have limited bond drawing capabilities. The actual bond drawing method is inefficiently implemented: the user must click a mouse button once at each end of each bond. Also, the user may not change a bond type while drawing. He or she must draw a second bond over the first in order to produce a double bond or enter a different bond mode in which each successive bond will be of the same type.

There are other shortcomings in bond drawing. While one may draw a bond at certain angles (angle constraints) or continuously at any angle, there is no provision for bisecting the angles of existing bonds. For labeling, the user must select a particular atom (usually located at the end of a bond) and type in the label. This cannot be performed "on the fly," e.g., while in a drawing mode with a mouse button depressed. Moreover, there is no provision for the automatic alignment of labels.

Computer-aided systems have automated the process of manipulating or transforming objects. Basic transformation techniques, including move, copy, re-orient, rotate, scale, or flip (mirror), are known in the art. However, current chemical systems have limited transformation facilities. For example, the user is only allowed to pivot (rotate transformation) a structure, such as a ring, around a point while it is being drawn. The user cannot create additional views or "reflections" while in a drawing mode, such as out-of-plane rotations of rings.

In prior systems, the user may draw chemical rings comprised of single and double bonds, for example, the Kekule structure for benzene. However, current implementations cannot recognize a closed chain of bonds as a ring. Without this ability, these systems cannot perform automatic ring operations, such as moving or "shifting" bonds within a ring.

Current systems for illustrating chemical structures offer significant advantages over freehand techniques. However, there are notable shortcomings. In particular, these systems fail to recognize or implement many techniques which are needed for the efficient illustration of chemical structures. The present invention provides novel methods and apparatus which fulfills this and other needs.

SUMMARY OF THE INVENTION

This invention provides a computer-aided chemical illustration system which provides novel methods and apparatus for creating and editing the structural formulas used in chemistry. The system includes: 1) efficient drawing of bonds; 2) drawing different bond types during a single mode; 3) determining bisect angles for bonds: 4) labeling atoms on the fly: 5) automatic alignment of atom labels; 6) custom alignment of atom labels; 7) changing the type, style, or orientation of an object while it is being drawn; 8) detection of ring structures; and 9) shifting bonds around on a ring.

DESCRIPTION OF THE PREFERRED EMBODIMENTS

Figure 1:
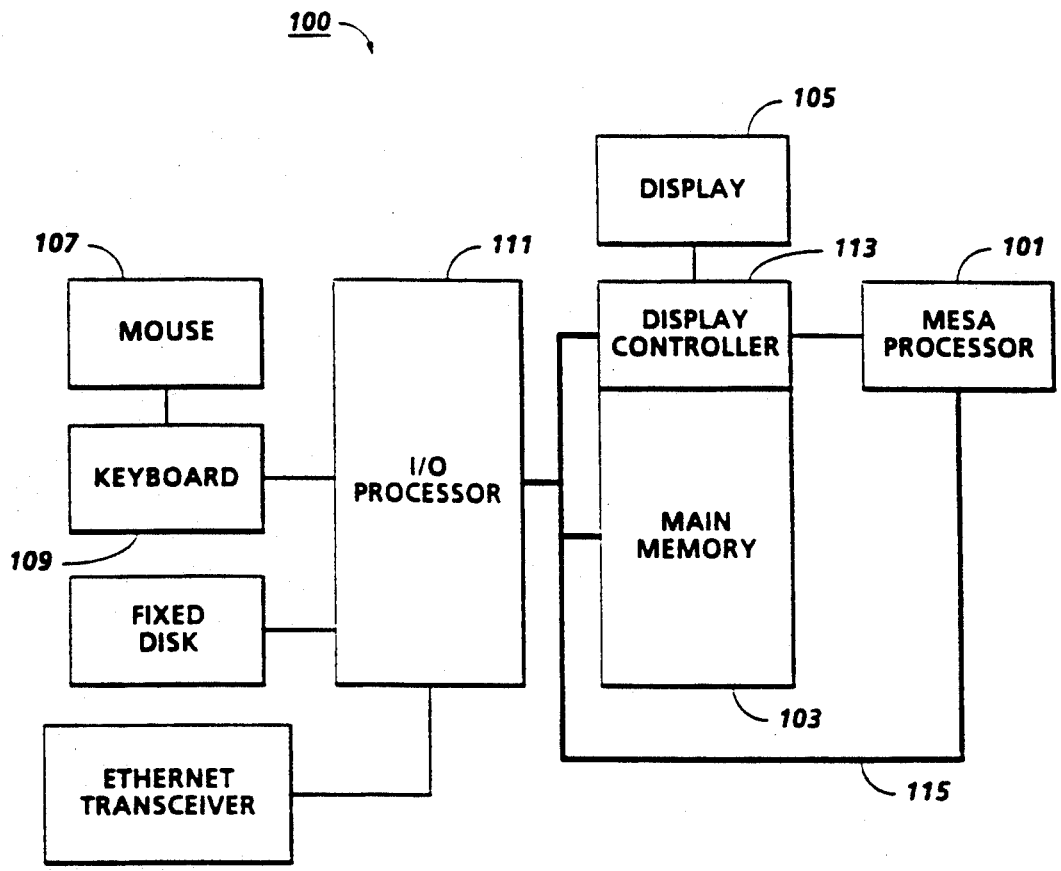
FIG. 1 is a simplified functional block diagram of a computer system in which the present invention may be embodied.

The invention may be embodied on a computer system such as the system 100 of FIG. 1, which comprises a central processor 101, a main memory 103, a display 105, a mouse 107, and a keyboard 109, with controllers 111, 113. The various components communicate through a system bus 115 or similar architecture. The user enters commands with the keyboard 109 and/or the mouse 107, while the computer communicates the result through the display 105, such as a cathode-ray tube or a printer. In the preferred embodiment, an appropriately programmed Xerox 6085 workstation is used.

In this interactive computer-aided chemical illustration system, the user constructs molecules on the display monitor 105 with the mouse 107. The system emulates the drawing tools which are typically available to scientists and technical writers, such as a polygon template, ruler, and pencil. Structural formulas are constructed from geometric objects which have precise mathematical definitions, and, thus, may be represented in the computer's memory 103. To draw a single bond, one need only specify its starting and ending points. Likewise, to draw a hexagon, one need only specify the location of two adjacent vertices on the hexagon. The ability of the system to precisely represent the various structural formulas and their inter-relationships provides anyone with the ability to create complex chemical illustrations.

The drawing of chemical bonds is crucial to the illustration of practically all molecules, and is, therefore, an important function of any chemical illustration system. The ability to specify only two control points for a bond is a major advantage that chemical illustration systems possess over freehand techniques.

However, prior systems have inefficiently implemented the means for placing these control points. Bond creation in such systems require users to specify both the starting and ending points for each and every bond drawn. This is required regardless of whether the starting point for a bond is the last control point placed, i.e., already available to the computer.

This duplication of effort is particularly noticeable for long acyclic chains. For example, in one such implementation, the user must click (depress) the mouse button at the starting point for the bond, drag (mouse button still depressed) the mouse to where the end of the bond will go, then release the mouse button to place the second control point for the end of the bond. The next bond is placed by clicking on the point last drawn, and again dragging the mouse to a new location. Thus, for n number of bonds, the user must specify 2n points, or two points for each bond. For example, to create a chain with three bonds, as found in butane, the user must specify six points. For a twenty-bond chain, forty points must be specified.

Figure 2:
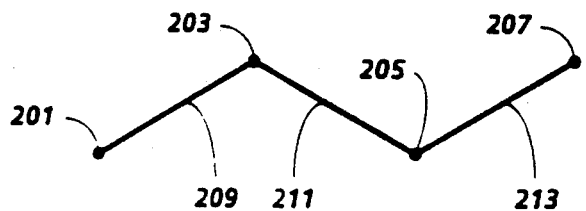
FIG. 2 illustrates the number of points required for a chain of bonds.

As FIG. 2 illustrates, there are only four points 201, 203, 205, 207 that are actually needed to specify three bonds 209, 211, 213, i.e., only n+1 points are needed to specify n number of bonds. Recognizing this, the preferred embodiment provides a user interface which allows for the efficient creation of bonds, especially when drawing multiple bonds.

Figure 3:
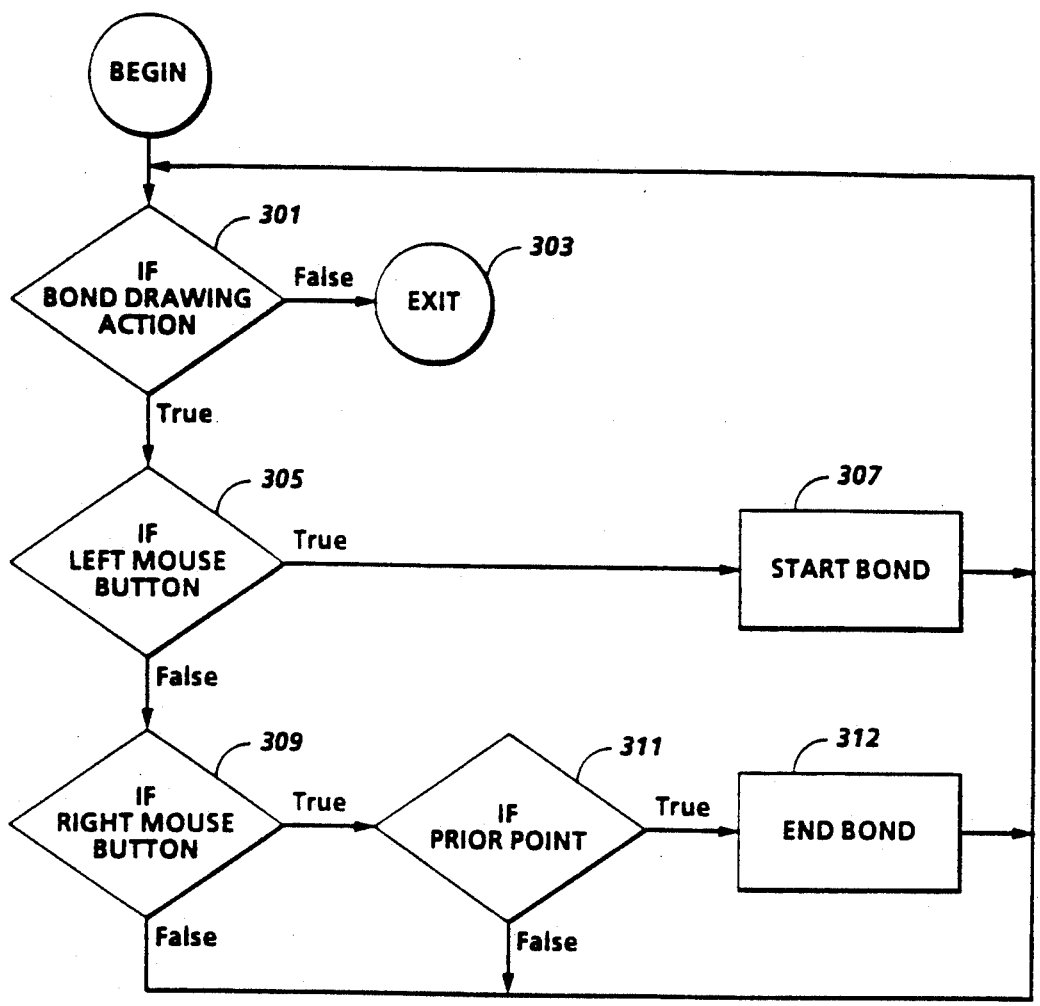
FIG. 3 illustrates the steps of bond drawing.

FIG. 3 illustrates the method for drawing bonds. Step 301 checks if the user enters a bond drawing command. Once the user invokes bond drawing, step 305 checks whether the left mouse button (LMB) is clicked or depressed. If this is true, then at step 307, a bond is started at that mouse location. If the LMB is not clicked, then step 309 checks whether the right mouse button (RMB) is clicked. If this is true, and a prior point is placed, step 311, then at step 312 the endpoint of the bond is placed at the corresponding mouse location. Since it takes two points to specify where to draw a bond, step 311 checks whether an endpoint is preceded by another prior point, which may be either a chain starting point (LMB) or a point on the chain (RMB).

Thus, it is apparent that the user may quickly create bonds by clicking the LMB to start and then click the RMB once for each bond. For example, to create an acyclic chain with three bonds, the user specifies four points by the following mouse clicks: LMB-RMB-RMB-RMB. Similarly, a twenty-bond chain drawn with bond drawing would only require that the user specify twenty-one points, not forty. New chains are automatically started each time LMB is clicked. In other words, when a user is drawing a chain with bond drawing, he or she may end the current chain and start a new one by moving the cursor to a new location and clicking the LMB.

Every bond has a set of properties that determines how the bond will look on the screen and on paper. Properties of a bond include: type, width, length, and spacing. In prior systems, changing bond properties was particularly cumbersome. For example, in order to change a single bond into a double bond, prior systems require the user to either draw a second bond over the first bond, or to enter a different bond mode in which each successive bond drawn would be of the same type.

In the preferred embodiment, a user interface is available for drawing bonds which allows the user to change bond properties while drawing. Specifically, dynamic "softkeys" are displayed which permit the user to change the parameters of a bond before, during, or after drawing a bond. Since this feature is concurrent with the bond drawing function, the user may change bond properties "on the fly," whether or not a mouse button is held down.

Figure 4:
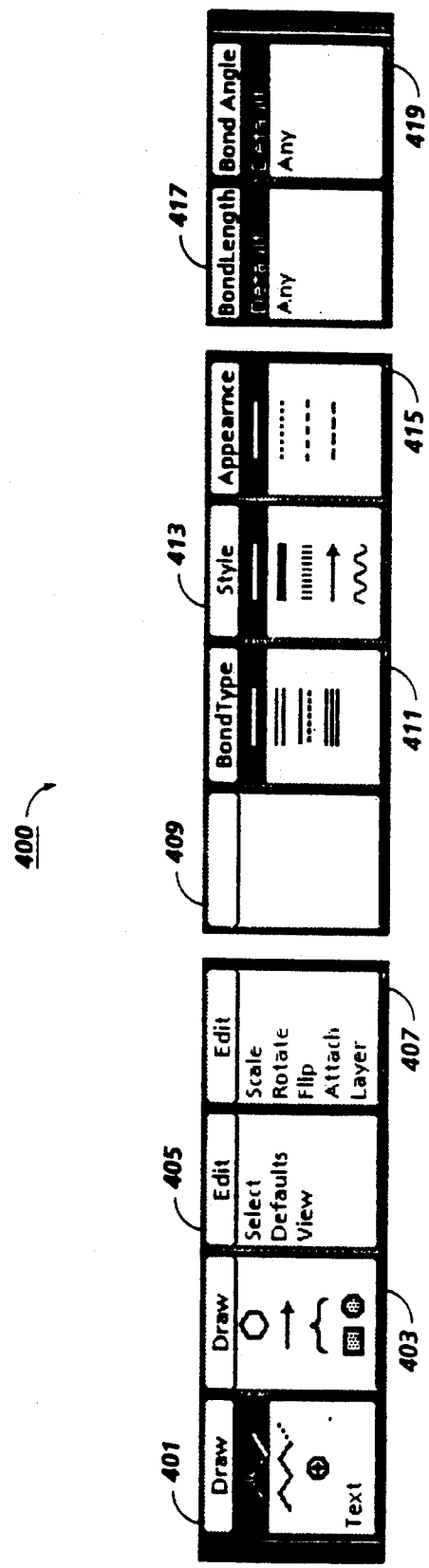
FIG. 4 illustrates the softkeys which are displayed with bond drawing.

FIG. 4 illustrates the softkeys which are displayed with bond drawing. The three softkeys for choosing bond types are the BondType 411, Style 413, and Appearance 415 softkeys. In the Draw softkey 401, the user selects the mode that he or she prefers, for example, single bond drawing or chain drawing. Softkeys 409-419 are updated to reflect the various bond properties that are available for change in the selected drawing mode. While drawing a bond, the user need only select a choice from the appropriate softkey to change a bond property on the fly.

Figure 5A:
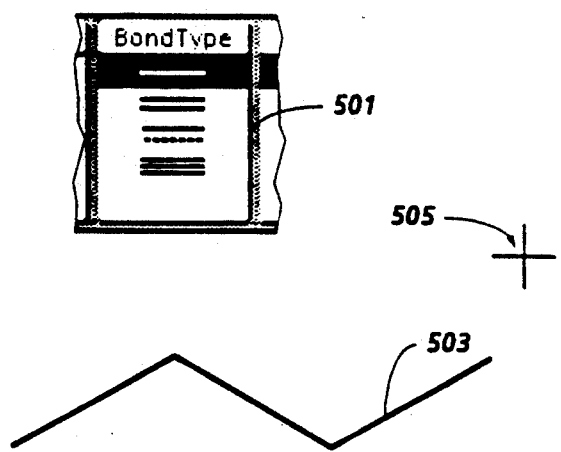
FIGS. 5A-C illustrate the operation of changing a single bond into a double bond.
Figure 5B:
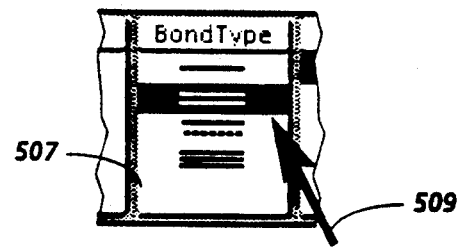
Figure 5C:
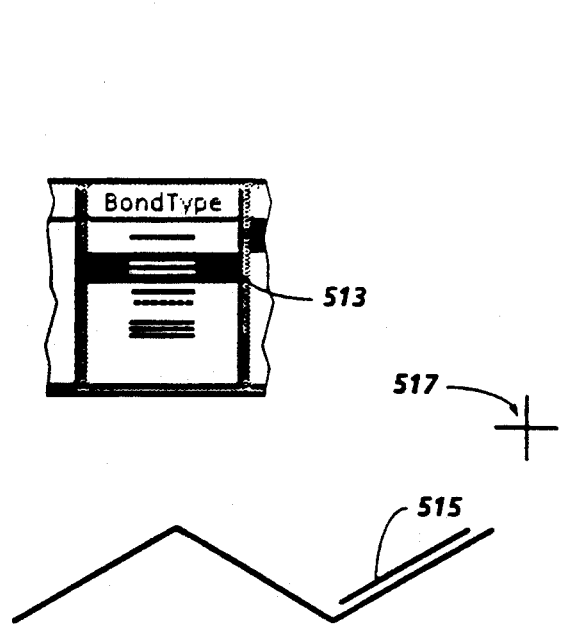

By way of illustration and not limitation, if the user draws a single bond and wishes to change it into a double or triple bond, he or she need only select the appropriate icon in the BondType softkey 411. FIGS. 5A-C illustrate the operation for changing a single bond into a double bond. In FIG. 5A, the user draws butane. The last bond drawn 503 automatically remains selected. The BondType softkey 501 is currently set to single bond. The mouse cursor 505 is used to select softkey options. In FIG. 5B, the user clicks the Double Bond icon in the BondType softkey with the mouse cursor 509, which changes temporarily to an arrow to facilitate pointing. The terminal butane bond is changed into a double bond 511. The user resumes bond drawing in FIG. 5C. The next bond will be a single bond (not shown).

Figure 6:
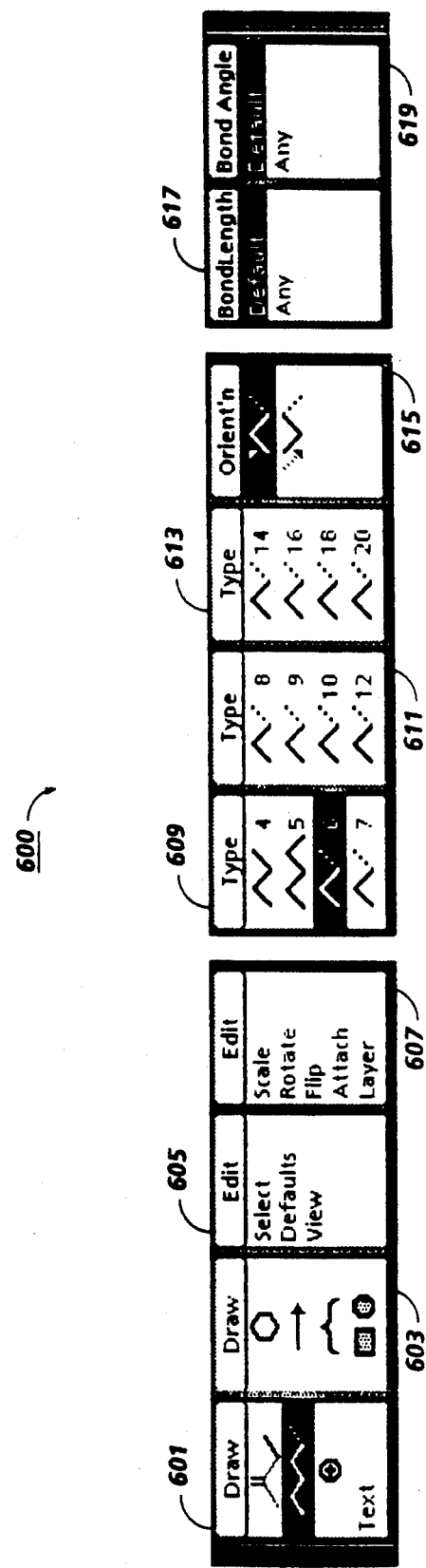
FIG. 6 illustrates the softkeys which are displayed with chain drawing.

As FIG. 6 illustrates, the user draws acyclic chains of predetermined length by choosing the Chain icon on the Draw softkey 601. The number of atoms is chosen from the Type softkeys 609, 611, 613, which change to reflect that the system is in Chain drawing mode. The user changes the orientation of a chain by choosing the appropriate icon on the Orient'n softkey 615.

Figure 7:
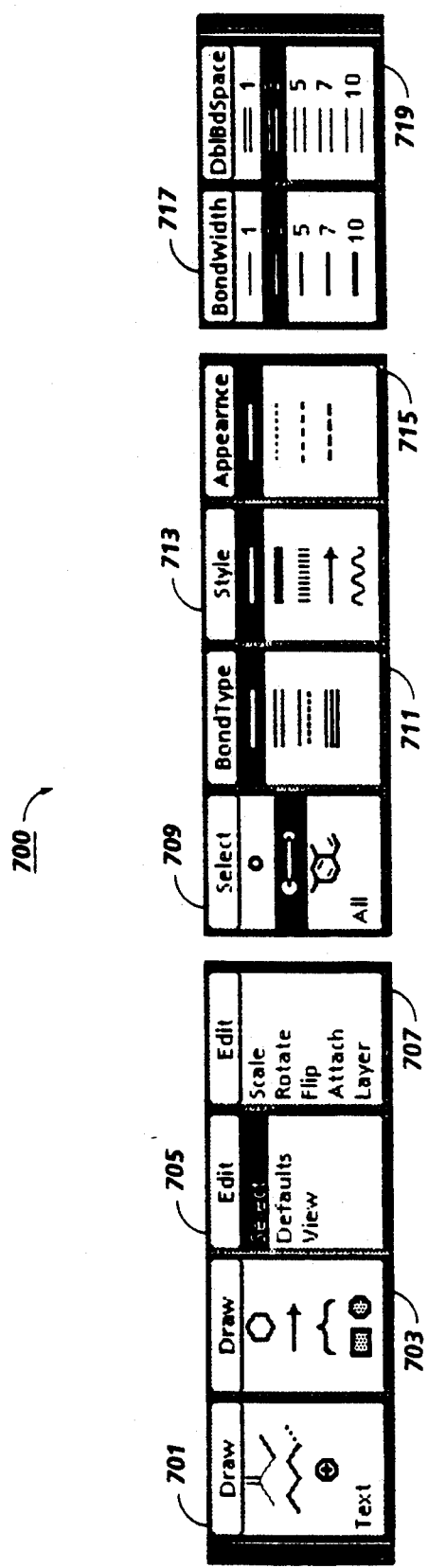
FIG. 7 illustrates the softkeys which are displayed when the user invokes the Edit Select mode.

When the user is drawing bonds, the last bond drawn automatically remains selected; when the user is drawing chains, the last plurality of bonds (chain) drawn remains selected; when a user exits bond drawing mode all the bonds that were drawn in the mode are selected. The system incorporates other methods for selecting objects for modification. As FIG. 7 illustrates, by choosing the Select icon in the Edit softkey 705, the user may select single or multiple atoms, bonds, and rings, or select all objects in a frame. This allows the user to perform an operation, such as deleting or changing bond type, on multiple objects.

Figure 8:
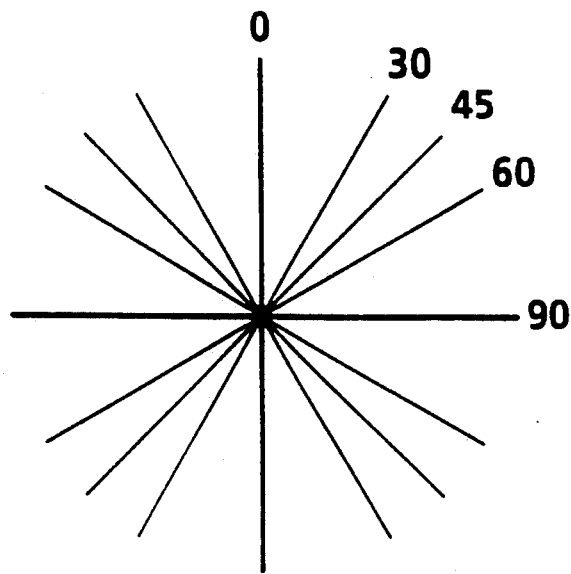
FIG. 8 illustrates the default constraint angles.

The preferred embodiment uses constraints to make the length and angles consistent in objects that the user draws and edits. As FIG. 8 illustrates, when an operation uses angle constraints, the default angles that are allowed are intervals of 30° and 45°, 30°, 45°, 60°, and 90° in a full circle. These angles are stored in an array:

ValidAngles : ARRAY [0 ... 18] OF Scalar=[0.0, 30.0, 45.0, 60.0, 90.0, 120.0, 135.0, 150.0, 180.0, 210.0, 225.0, 240.0, 270.0, 300.0, 315.0, 330.0, 360.0, 360.0, 360.0];

The 360° angle is repeated for the last three positions (ValidAngles[16] to ValidAngles[18]) to allow for the insertion of two more angles into the array. Intermediate angles are not allowed unless the user chooses to override the angle constraints.

Figure 9:
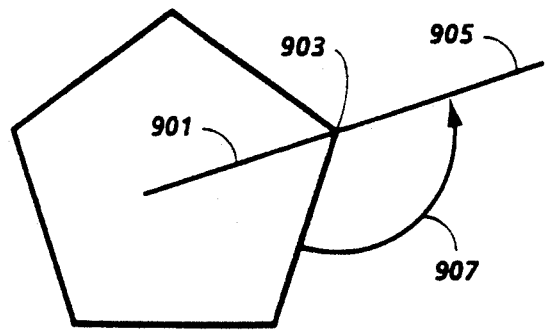
FIG. 9 illustrates the use of bisect angles.

When a user draws a chemical object from a point where two bonds join, the system allows two additional angles—the bisect angles. FIG. 9 illustrates the use of bisect angles. For the user to correctly place the bond 905 on the ring at atom 903, the bond must be in a location such that it bisects 907 the angles formed by the bonds which meet at the atom 903. The system determines this bisect angle and its extension (bisect angle+180°), and includes them as valid constraint angles.

Figure 10:
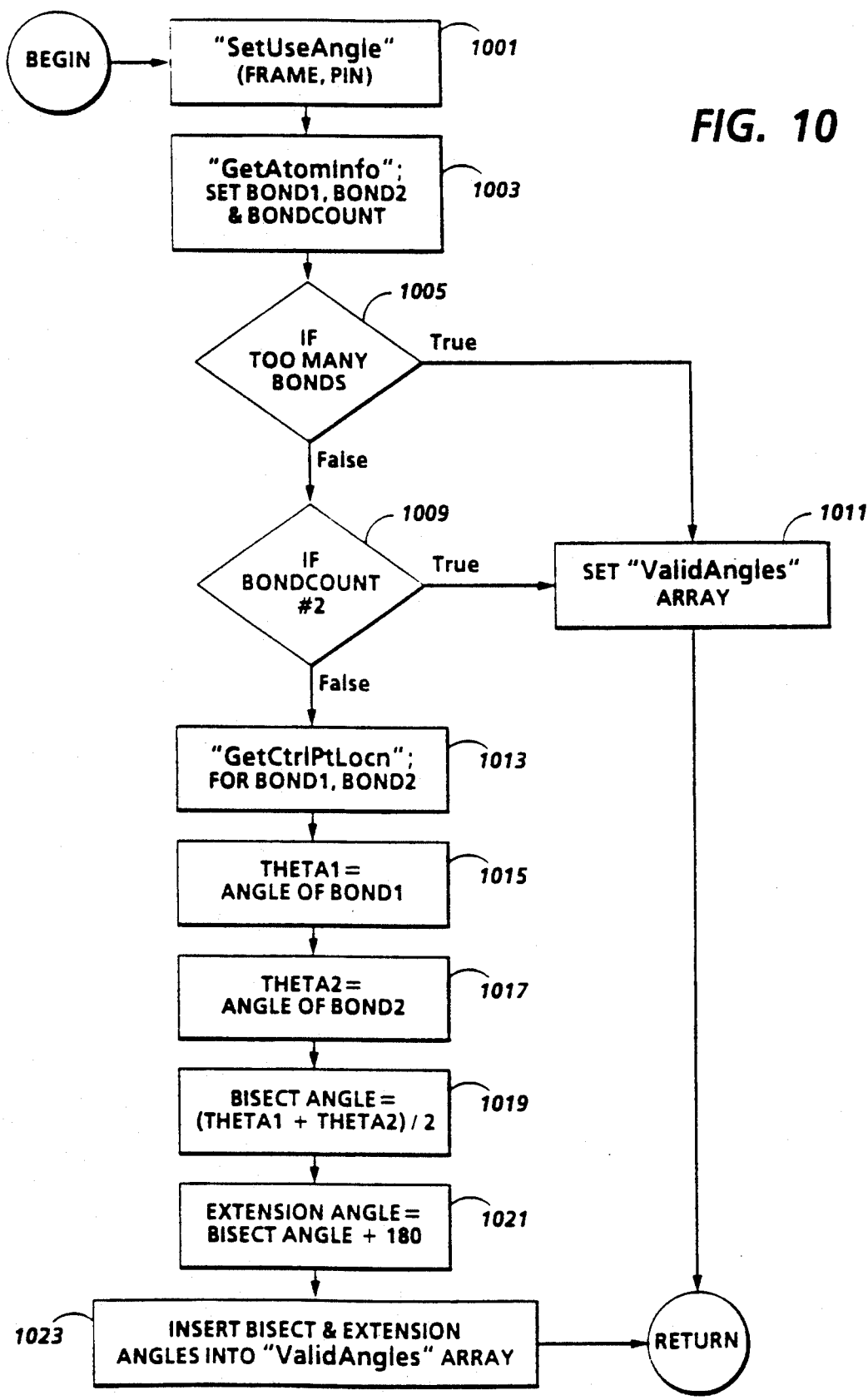
FIG. 10 illustrates the method for determining bisect angles.

As FIG. 10 illustrates, the method for determining the bisect angles at a user specified point comprises the following steps. In step 1001, the SetUseAngle procedure is called with the parameters "frame" and "pin." The frame variable specifies the current rectangular drawing area within a document window. Its properties include margins, alignment, captions, and borders. The pin variable specifies the current mouse location. At step 1003, GetAtomInfo is called. This procedure examines the current mouse location in the frame (pin and frame variables) and returns the atom information at that point. The atom information further comprises atom (a record of type Atom) and numberOfBonds at atom. The Atom record comprises a list of bonds connected at atom's location (at least one), in addition to other attributes. The numberOfBonds is returned to MyTakeBond, a locally defined procedure. MyTakeBond sets the local variables bond1, bond2, and bondCount from the Atom data. bond1 and bond2 store the bonds found at the pin, each comprising two control points and properties that define a bond.

If at step 1005, there are too many bonds (tooManyBonds =true), or at step 1009 bondCount is not equal to two, the procedure returns without adding the bisect angles to the ValidAngles array, step 1011. In other words, bisect angles cannot be computed if there are not two bonds (angles). In this case, at step 1011 the procedure sets the ValidAngles array without inserting bisect angles. However, if bondCount is equal to two in step 1009, then at step 1013 GetCtrlPtLocn gets the bond control points for bond1 and bond2, and stores them in local variables. At step 1015, the angle (slope) of bond1 is computed from its two control points, locA1 and locA2, and assigned to the local variable theta1. In a similar fashion, the angle of bond2 is computed from its control points, locB1 and locB2, in step 1017, and assigned to theta2. However, at step 1017, the control points of bond2 are first compared with those of bond1 so that bond2's angle is calculated relative to the intersection of bond1 and bond2, i.e., where locAn=locBn.

At step 1019, the bisect angle is computed by averaging theta1 and theta2. The 180° extension of the bisect angle is computed in step 1021 by adding 180 to the bisect angle. Finally, at step 1023, the bisect and extension angles are inserted into the ValidAngles array, and the procedure returns. Now the ValidAngles array contains the default angles plus the bisect angles (bisect and extension angles) for the atom at the mouse location.

An atom label is text that appears at an atom site. It identifies the atom. The label can be an element name, for example C, H, S, N, or Cl. It can also be shorthand for a chemical group, such as COOH, Et, Ph, or $CH_2$, or even a chain of atoms, such as $HOCHCH_2OH$. In fact, the label can be anything that the user types.

Figure 11:
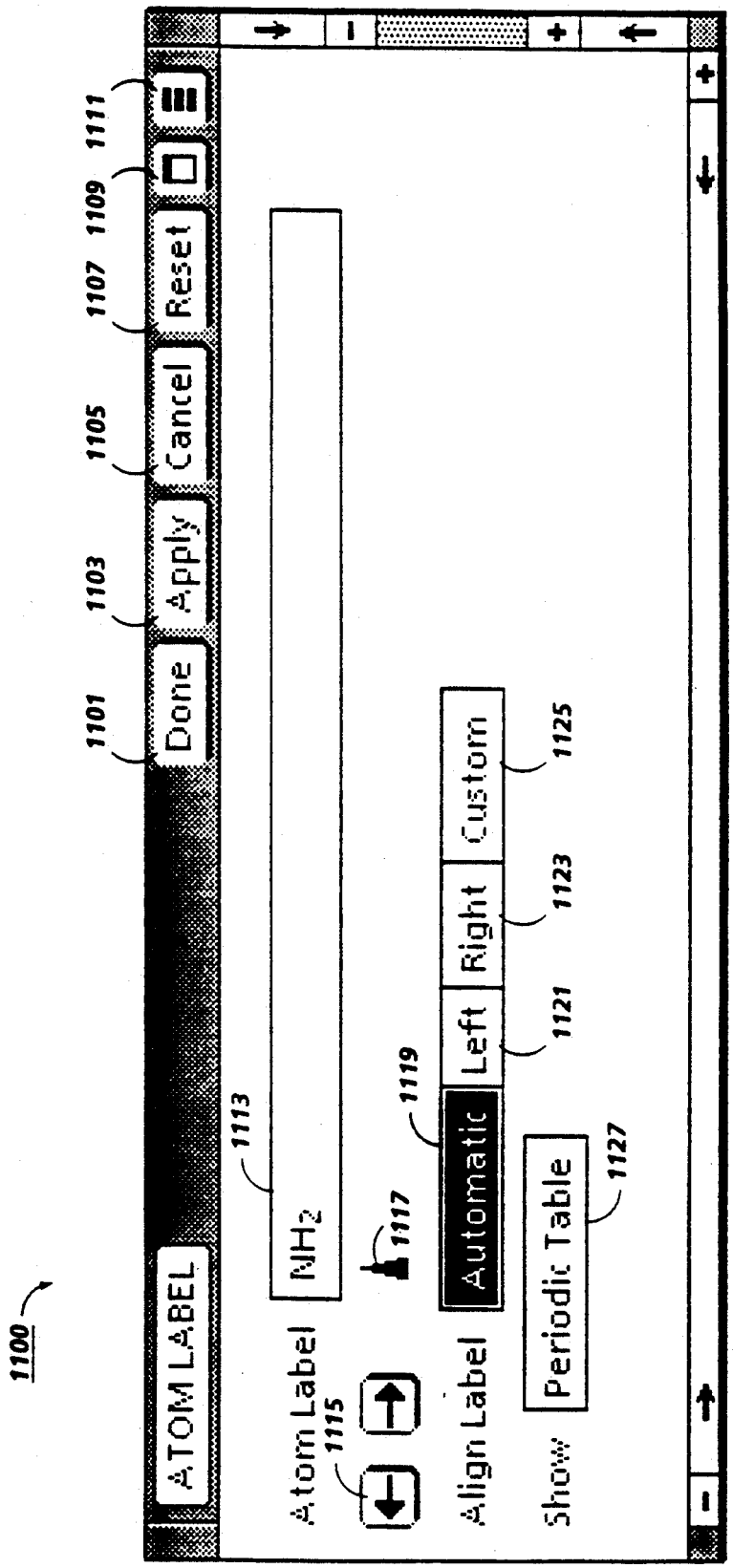
FIG. 11 illustrates the Atom Label window.

In prior systems, the user can label an atom only after selecting it. The present invention, however, allows the user to label atoms on the fly, i.e., while a bond is being drawn. As FIG. 11 illustrates, a special Atom Label window 1100 is used. While in a bond drawing mode, any character typed by the user appears in the text window 1113. Numbers are automatically subscripted, unless the user specifies otherwise. After entering a label, the user applies it to an atom by choosing the Apply selection 1103, pressing the Next key on the keyboard, or depressing a mouse button. After the label is applied, it disappears from the text window 1113 so that the user can type in the next label. The text window 1113 is linked with a periodic chart. By selecting Periodic Table 1127 from the Atom Label window 1100, the user may display the periodic table of elements.

The preferred embodiment provides for the automatic alignment of atom labels. The characters of a label are positioned to the left or the right of an atom based on the bonds connected to that atom. In other words, the label is automatically aligned relative to the bonds so that the bonds are not obscured. This is performed automatically while drawing and performing transformations. Prior systems allow the user to choose and modify the alignment of the label, but they do not provide automatic alignment.

Figure 12:
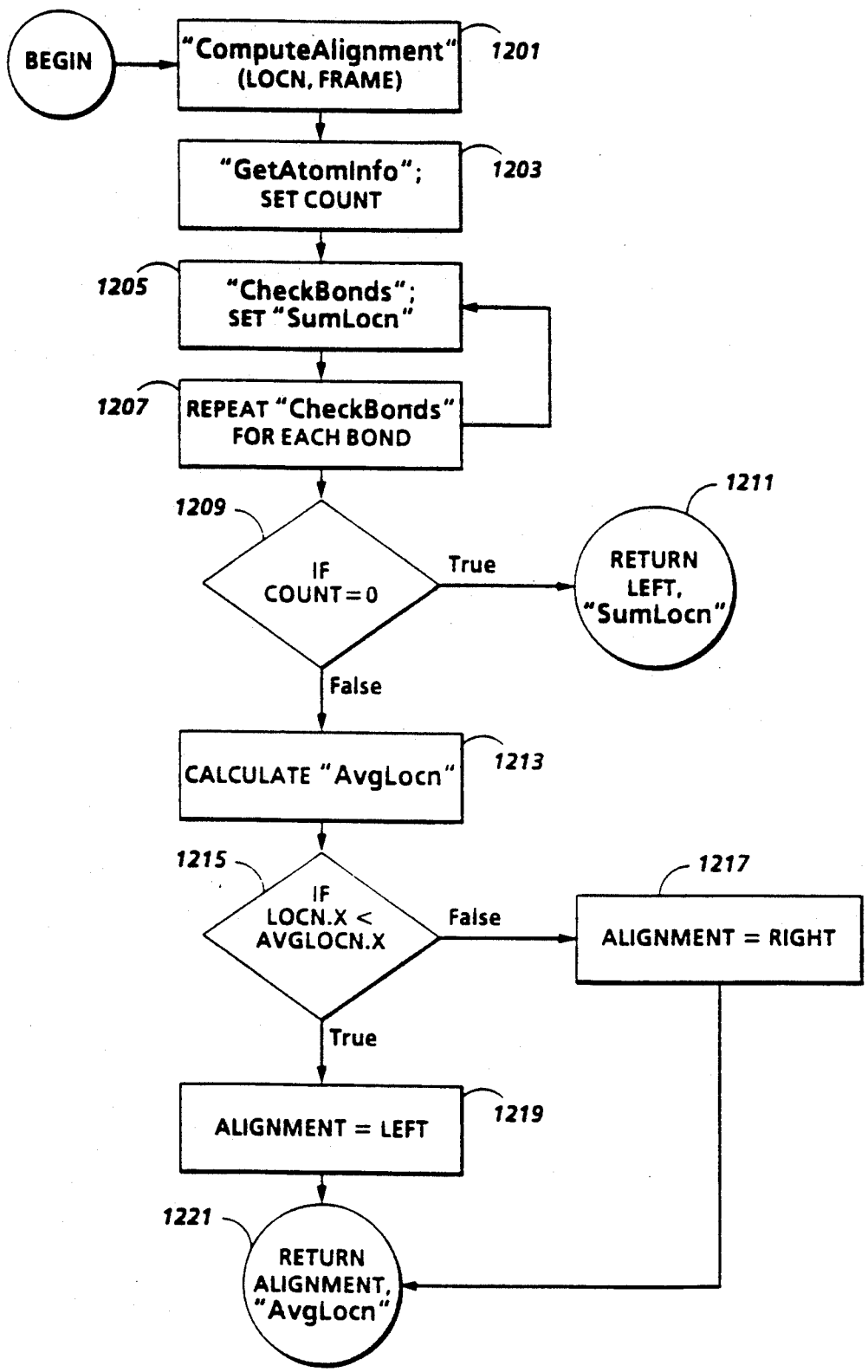
FIG. 12 illustrates the method of auto-label alignment.

FIG. 12 illustrates the steps of auto-label alignment. The procedure ComputeAlignment determines an alignment direction, right or left, after examining the length and direction of bonds entering an atom. In step 1201, ComputeAlignment is called with the parameters locn and frame. The location of the atom to be labeled is passed to locn; the current frame is passed to frame. At step 1203, the procedure calls GetAtomInfo which returns the bond properties and number of bonds for the atom at locn. The local procedure, CheckBonds, in step 1205, is called to examine each bond that was returned by GetAtomInfo. The endpoint of each bond that is not at locn is added to the local variable sumLocn. If no bonds were found at step 1209, then ComputeAlignment sets alignment to left. Otherwise, at step 1213, the procedure calculates the average location of the bonds found. Average location or avgLocn is calculated by dividing sumLocn by count. At step 1215, if avgLocn is to the left of locn, then alignment is set to right. Otherwise, in step 1217, alignment is set to left. In other words, the label will be aligned opposite to where most of the bonds are.

After the alignment is calculated, the label is applied to the atom location. If alignment is left, the first letter in the label is placed at the atom location, the remainder lying to the right of the atom. However, if alignment is right, the last uppercase letter in the label is placed at the atom location, and the remainder lying to the left of the atom.

Figure 13A:
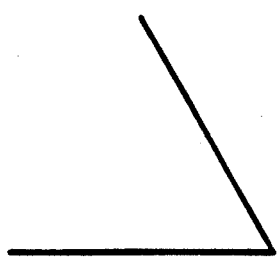
FIGS. 13A-D illustrate the operation of auto-label alignment.
Figure 13B:
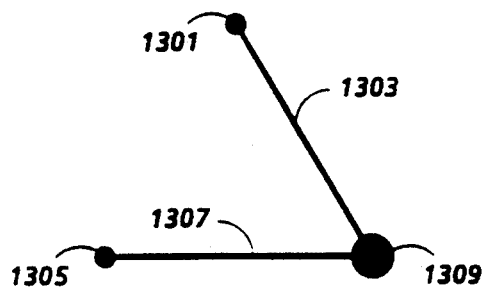
Figure 13C:
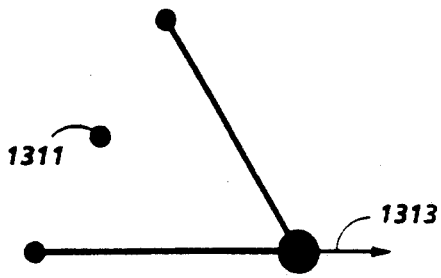
Figure 13D:
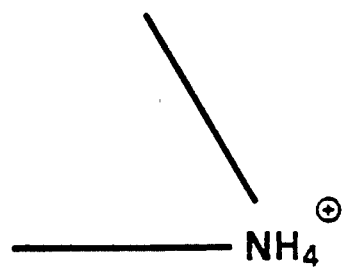

FIGS. 13A-D illustrate the operation of auto-label alignment. FIG. 13A represents two bonds which join an unlabeled atom at 60°. FIG. 13B illustrates the endpoints 1301, 1305 for the bonds 1303, 1307 which join at atom 1309. Of the two points 1301, 1309 which define bond 1303, only the endpoint 1301, which is not at locn 1309, is added to sumLocn. Similarly, only the distal endpoint 1305 of the second bond 1307 is added to sumLocn. avgLocn is computed by dividing sumLocn by count (two bonds here). FIG. 13C graphically illustrates the position of avgLocn 1311 which is an average location for the endpoints. In this example, since avgLocn is to the left of locn, i.e., avgLocn.x<locn.x, alignment is set to right 1313. FIG. 13D illustrates that the atom label is properly positioned.

Auto-label alignment also calculates proper alignment for stacked labels. For example, if a label's height is greater than its width, i.e., more vertical, then the label is vertically aligned. As with horizontal alignment, the system looks at the bonds entering the atom to determine where to place the vertically aligned label. This is done by determining if avgLocn is above (up) or below (down) locn. If avgLocn is up, i.e., avgLocn.y>lcon.y, the label is placed below; otherwise, it is placed above. It is apparent that there are four label placement combinations:

1) width>height, locn.x<avgLocn.x (right): horizontal and left;
2) width>height, locn.x>avgLocn.x (left): horizontal and right;
3) width<height, locn.y<avgLocn.y (up): vertical and down;
4) width<height, locn.y>avgLocn.y (down): vertical and up.

Figures 14A, 14B:
FIGS. 14A-14B illustrate horizontal and right, and vertical and down label alignments.

FIG. 14A illustrates horizontal and right alignment, while FIG. 14B illustrates vertical and down alignment.

In addition to auto-label alignment, the present invention allows the user to make custom alignments. To invoke custom label alignment, the user selects the Custom icon (FIG. 11, 1125) in the Atom Label window 1100 with the mouse cursor. This enables the alignment arrows icons 1115 and the alignment caret 1117 (they are also enabled when they are initially selected). Fine-grain adjustment of the label alignment is accomplished by selecting the appropriate arrow 1115 with the mouse.

The system provides for the ability to change the orientation or style of an object being drawn. For example, the user may choose different reflections while drawing a ring. The user may even change reflections while depressing a mouse button by choosing the appropriate softkey with the keyboard.

In the preferred embodiment, the user may draw a chemical structure by placing a single bond. From this bond, a template is used to draw a ring or chain which corresponds to the currently chosen softkey. To change a structure's type or style, the user need only select a different softkey. In turn, the prior structure is discarded, and a new structure is displayed from the new template.

Figure 15:
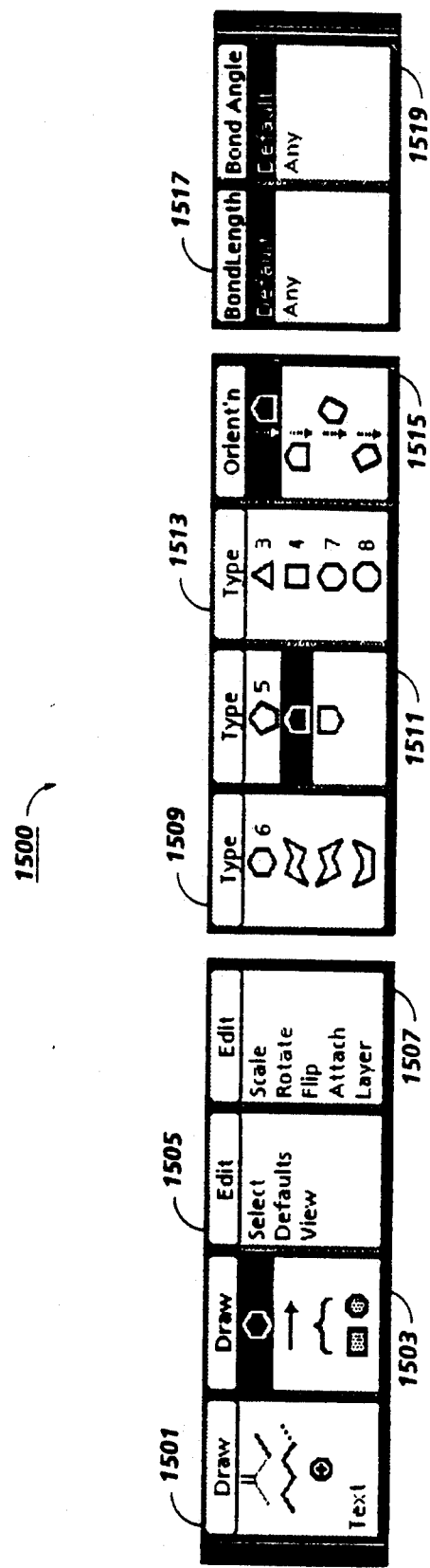
FIG. 15 illustrates the softkeys which are displayed with ring drawing.

FIG. 15 illustrates the softkeys which are displayed with ring drawing. In the Draw softkey 1503, the user selects a drawing mode, for example, ring drawing. Softkeys 1509-1519 are updated to reflect the various types, orientations, and properties that are available for change in the selected drawing mode. There are three softkeys 1509, 1511, 1513 for choosing ring type. While drawing a ring, the user need only select a choice from the appropriate softkey to change a ring property on the fly.

By way of illustration and not limitation, if the user desires to draw a five-member ring, he or she need only draw a single bond, i.e., specify two control points, and choose the softkey 1511 with five-member rings. By using the Type 1509, 1511, 1513 and Orientation 1515 softkeys, the user may instantly change the ring type or orientation. No additional steps are needed.

Figure 16A:
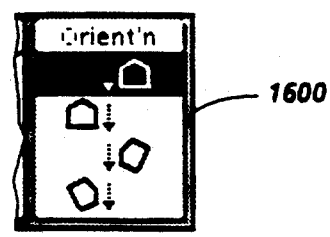
FIGS. 16A-E illllustrate the operation of changing the orientation of a "house" ring.
Figure 16B:
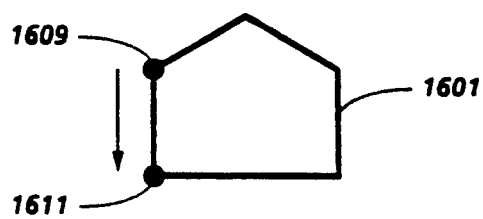
Figure 16C:
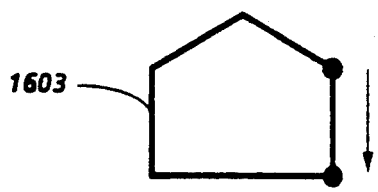
Figure 16D:
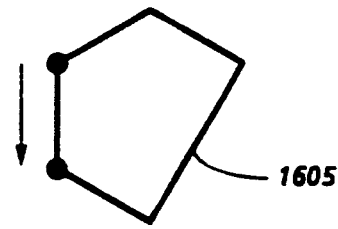
Figure 16E:
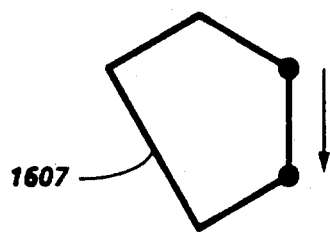

FIGS. 16A-E illustrate changing the orientation of a five-member or "house" ring. In FIG. 16A, the Orient'n softkey is set in its default position. FIG. 16B illustrates that the ring 1601 drawn is lying to the right and upright from the control points 1609, 1611 placed by the user. FIG. 16C illustrates the mirror image 1603 of the ring 1601, which is constructed by the user selecting the second icon in the Orient'n softkey 1600. FIGS. 16D-E illustrate other reflections 1605, 1607 that are possible for this ring. This technique is easily adapted to other chemical structures, for example, flipping acyclic chains (FIG. 6, 615), changing the shape of a ring (FIG. 15, 1509), or changing the number of members in a ring (FIG. 15, 1513).

The present invention has the ability to detect ring structures by employing a RingDetection function. Rings are polygonal-shaped objects used in structural formulas to illustrate ring-shaped molecules. For example, a triangle is used to represent the structure of cyclopropane. Both the molecule and its structural formula are planar, with vertices of 60°. Likewise, a hexagon is used to represent benzene.

However, it is understood that rings may be used to represent chemical ring structures which are not necessarily planar. For example, a square is used to represent cyclobutane, while a simple hexagon is used to represent cyclohexane; neither molecule is planar. Occasionally other two-dimensional objects, such as boats or chairs, are used to emphasize the three-dimensional nature of non-planar ring structures. Sometimes the placement of bonds will distinguish between planar and non-planar ring structures. A hexagon drawn with three evenly spaced double bonds indicates that it is the Kekule's structural formula for benzene. Of course, benzene does not consist of alternating single and double bonds, but instead consists of uniform aromatic bonds. Acyclic chains and other non-cyclic chemical structures are not rings.

The present invention automatically recognizes rings. In order to be recognized, a ring must be a closed chain comprising three to eight bonds. For example, both benzene and cyclohexane will be properly recognized as six-member ring structures, even though only the former is a planar structure. A ring is detected even if it is part of a larger structure, including other rings.

There are several advantages to recognizing rings. The location of the ring's interior may be determined. This aids in the proper placement of additional bonds and labels. For example, if a single bond of a ring is converted into a double bond, it should be drawn so that the additional bond is in the interior of the ring.

Another advantage is that the ring style may be "normalized" so that it is consistent with other rings of that type. A recognized ring is compared to known ring types by using MemberRingStyle templates. When a ring is matched to a template, its data structures are normalized to produce a uniform appearance, i.e., one that is not affected by variances from bond drawing. For example, a double bond with one short side will have the short side to one side or the other depending on the direction in which it is drawn. Ring detection adjusts for these variabilities to yield consistent ring styles.

Figure 17:
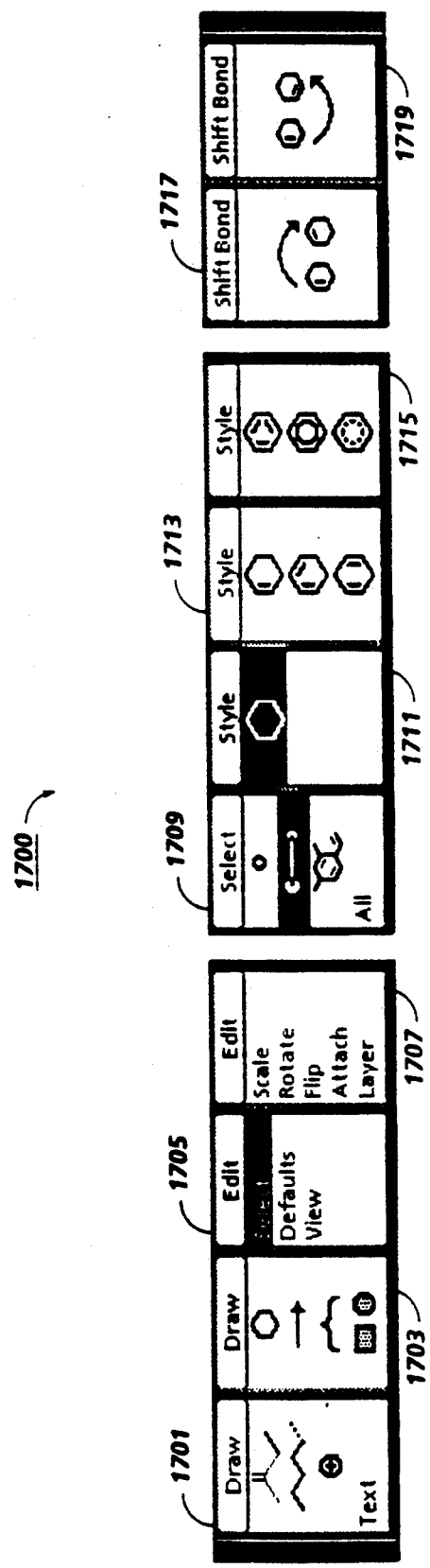
FIG. 17 illustrates the softkeys which are displayed for six-member rings.

As FIG. 17 illustrates for a six-member ring, when an extended selection of bonds comprising a ring is made, the softkeys 1711, 1713, 1715, 1717, 1719 depict a ring with the correct number of sides regardless of the geometry of the selection. Thus, all five and six-member rings will show the equilateral style on the softkeys. From the ring softkeys (FIG. 15, 1500; FIG. 17, 1700), the user may change ring types 1509, 1511, 1513, styles 1711, 1713, 1715, and orientation 1515, or even shift bonds 1717, 1719 within a ring. However, changes to ring types or orientation may only be performed before or during drawing. Ring style can only be changed after a ring is drawn. If the extended selection is less than or more than a ring, the bond softkeys (FIG. 4, 411, 413, 415, 417, 419) appear.

The mechanism by which rings are detected, the RingDetection procedure, will now be described in detail. It is helpful, initially, to study the data structures used by RingDetection. SingleDouble is an enumerated variable which specifies the types of bond that occur in a ring:

SingleDouble: TYPE = {single, double, other};
RingStyle is an array of SingleDouble, i.e., it specifies an array of bonds which may be single, double, or any which combine to form a ring:

RingStyle: TYPE = ARRAY[0 ... 8] OF SingleDouble;

RingStyleArray is used to store the RingStyle, which defines the different bond styles (indicated by SingleDouble) for a given ring style (RingStyle):

RingStyleArray: TYPE = ARRAY[0 ... 8] OF RingStyle;

After defining these data structures, the templates for three-member to eight-member rings may now be defined as follows:

```
threeMemberRingStyle: RingStyleArray = [
[single, single, single, other, other, other, other, other],
[single, single, double, other, other, other, other, other],
NullStyle, NullStyle, NullStyle, NullStyle, NullStyle, NullStyle];
fourMemberRingStyle: RingStyleArray = [
[single, single, single, single, other, other, other, other],
[single, single, single, double, other, other, other, other],
[single, double, single, double, other, other, other, other],
NullStyle, NullStyle, NullStyle, NullStyle, NullStyle];
fiveMemberRingStyle: RingStyleArray = [
[single, single, single, single, single, other, other, other],
[single, single, single, single, double, other, other, other],
[single, double, single, single, double, other, other, other],
NullStyle, NullStyle, NullStyle, NullStyle, NullStyle];
sixMemberRingStyle: RingStyleArray = [
[single, single, single, single, single, single, other, other],
[single, single, single, single, double, single, other, other],
[single, single, double, single, double, single, other, other],
[single, double, single, single, double, single, other, other],
[double, single, double, single, double, single, other, other],
NullStyle, NullStyle, NullStyle];
```

```
sevenMemberRingStyle: RingStyleArray = [
 [single, single, single, single, single, single, single, other],
 [single, single, single, single, single, double, single, other],
 [single, single, single, double, single, double, single, other],
 [single, single, double, single, single, double, single, other],
 [double, single, double, single, single, double, single, other],
 NullStyle, NullStyle, NullStyle];
eightMemberRingStyle: RingStyleArray = [
 [single, single, single, single, single, single, single, single],
 [single, single, single, single, single, single, double, single],
 [single, single, single, single, double, single, double, single],
 [single, single, single, double, single, single, double, single],
 [single, single, single, double, single, single, double, single],
 [single, single, double, single, single, double, double, single],
 [single, single, double, single, double, single, double, single],
 [double, single, double, single, double, single, double, single],
 NullStyle];
```

It should be noted that NullStyle is a RingStyle with all its elements set to other.

The above templates are referenced by ringStyleTable, which is an array that stores the number of types (noTypes), the number of bonds (noBonds), and the style of the ring (RingStyleArray). ringStyleTable is constructed by the following declarations:

```
RingStyleTableEntry: TYPE = RECORD[
noTypes: CARDINAL 0,
noBonds: CARDINAL 0,
style: RingStyleArray];
ringStyleTable: ARRAY RingType OF RingStyleTableEntry = [
 [2, 3, threeMemberRingStyle],
 [3, 4, fourMemberRingStyle],
 [3, 5, fiveMemberRingStyle],
 [3, 5, fiveMemberRingStyle],
 [3, 5, fiveMemberRingStyle],
 [5, 6, sixMemberRingStyle],
 [5, 7, sevenMemberRingStyle],
 [7, 8, eightMemberRingStyle],
 [5, 6, sixMemberRingStyle],
 [5, 6, sixMemberRingStyle],
 [5, 6, sixMemberRingStyle],
 [5, 6, sixMemberRingStyle]];
```

Thus, it is apparent that threeMemberRingStyle has three bonds and two types or combinations of bonds—single, single, single or single, single, double.

Figure 18A:
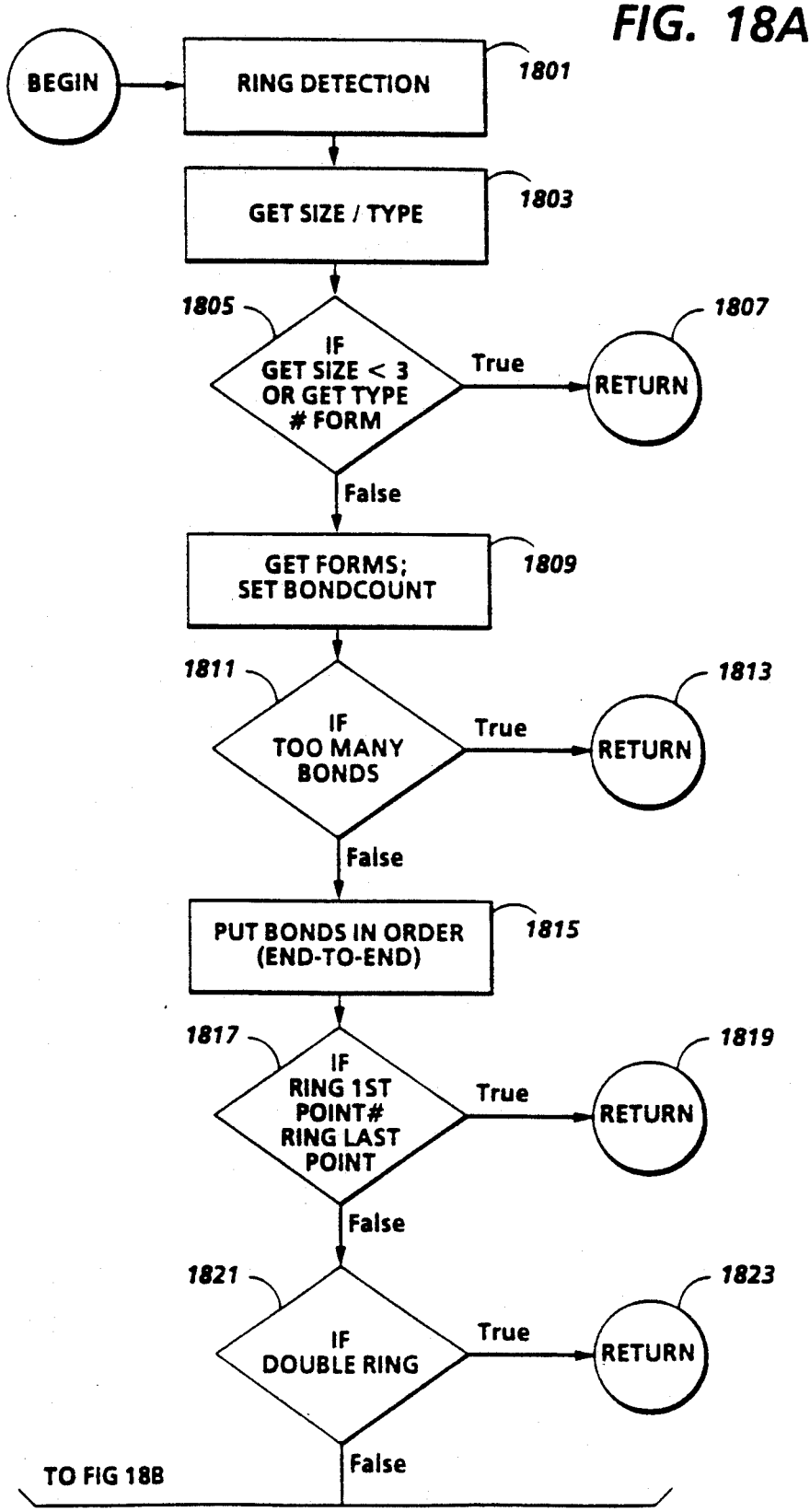
FIGS. 18A-B illustrate the method of ring detection.
Figure 18B:
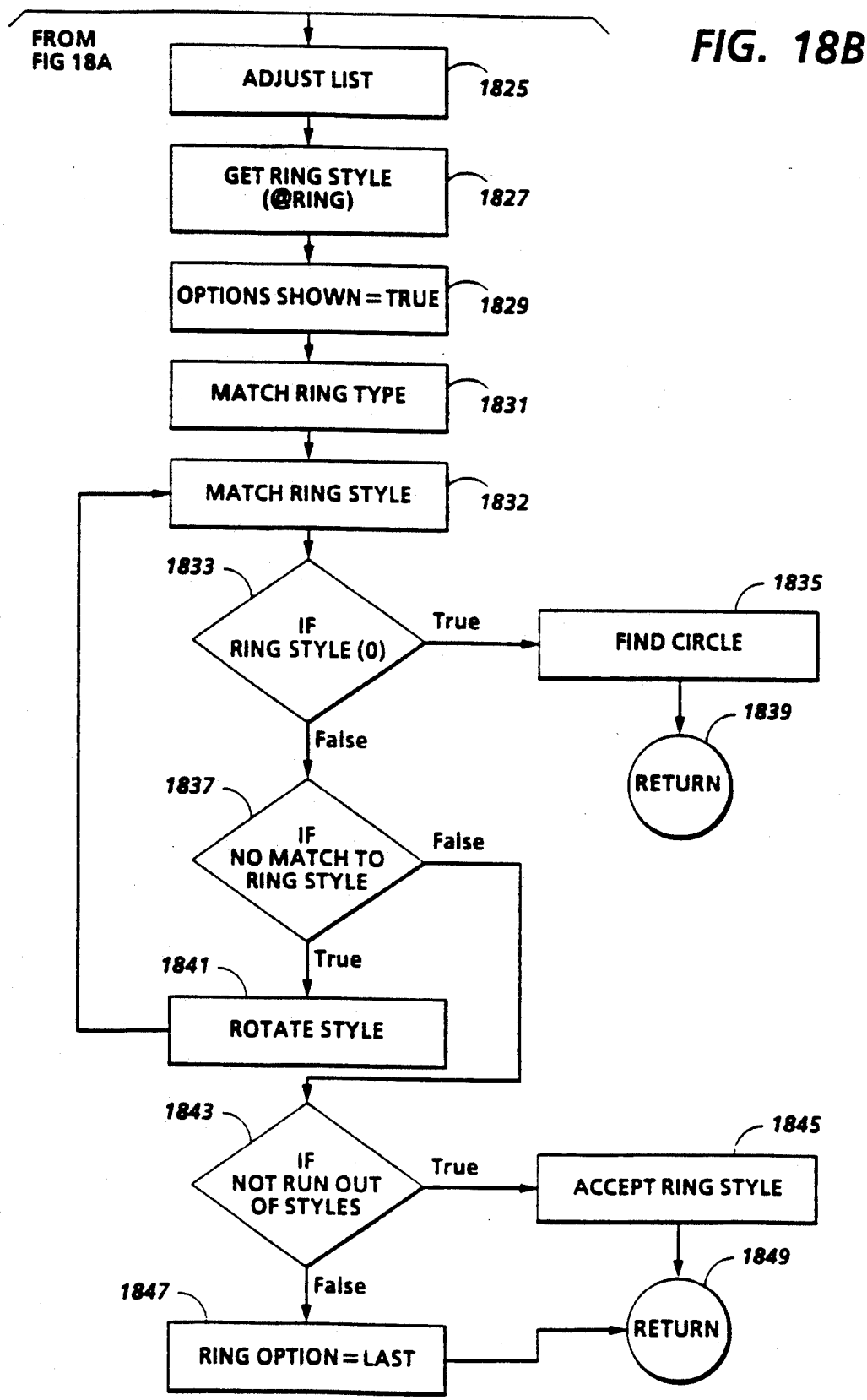

FIG. 18A-B illustrates the RingDetection procedure. At step 1801, RingDetection is called; there are no parameters to pass to RingDetection. At step 1803, the GetSize and GetType functions are called. GetSize returns the number of objects in selection. GetType specifies what objects (form or ctrlPt) are in selection. At step 1805, if there is either less than three objects or no form in selection, then there cannot be a ring in selection, and the procedure returns. At step 1809, GetForms, a locally-declared procedure, is called which counts the number of bonds for the object or form in selection. The number of bonds found is stored in bondCount, a local variable. At step 1811, if bondCount is tooManyBonds, the procedure returns. Otherwise, there is a form and it has a valid number of bonds.

At step 1815, the bonds are arrange in order, end-to-end. In RingDetection, each bond is stored into a "ring" array. Sorting the order of the bonds is a simple matter of comparing the control points of each bond, stored in ring[i,j], with the control points of other bonds. When two separate bonds share the same control point, they must be connected. These connections are identified and ordered. After all the bonds are sorted into order, step 1817 checks to make sure that the first point and the last point are the same. If they are not, then the "ring" is not closed, and the procedure returns at step 1819. In addition, step 1821 checks for double rings, such as found in naphthalene, by confirming that each atom (vertex) of a ring only has two bonds in selection. RingDetection is only interested in identifying single rings. If a single ring is not found at step 1821, the procedure returns at step 1823.

Figure 19A:
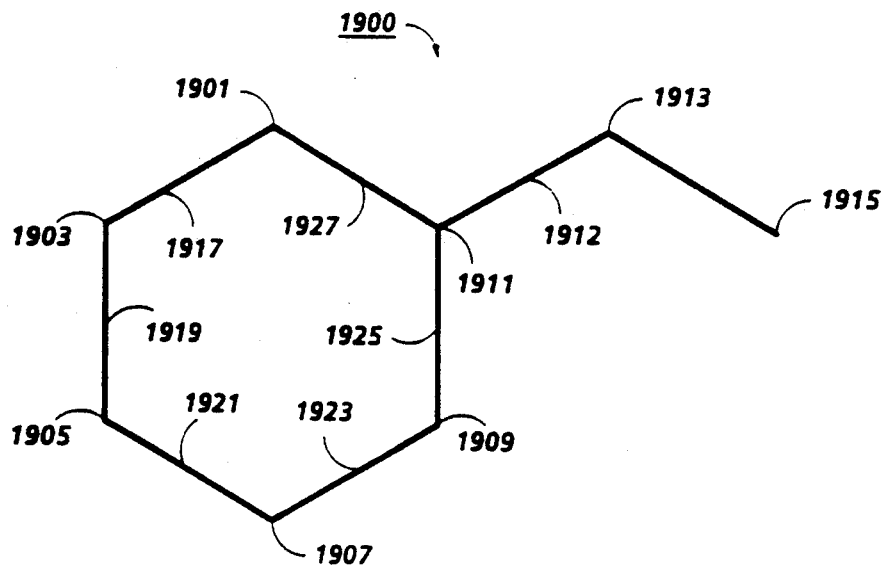
FIGS. 19A-B illustrate valid and invalid rings.
Figure 19B:
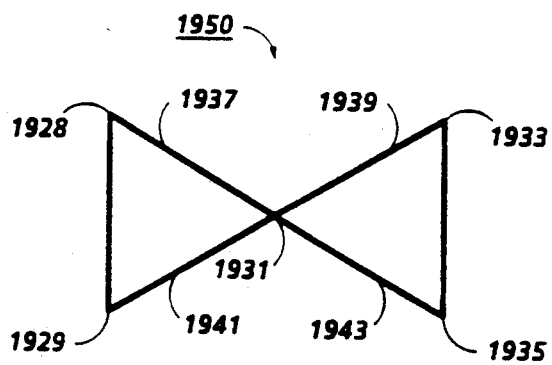

FIGS. 19A-B illustrate structures 1900, 1950 that consist of more than a single ring. In FIG. 19A, if the ring atoms (vertices) 1901, 1903, 1905, 1907, 1909, 1911 are in selection, and thus bonds 1917, 1919, 1921, 1923, 1915, 1927 are selected, then a valid ring is identified. However, if chain atom 1913 is included in selection, and thus bond 1912 is selected, then there is no single ring. Step 1821 recognizes this by finding greater than two bonds, i.e., three bonds 1927, 1925, 1912, connecting to atom 1911. Similarly, the "bowtie" molecule 1950 is not a single ring if all atoms 1927, 1929, 1931, 1933, 1935 are in selection since the center atom 1931 has four bonds 1937, 1939, 1941, 1943 connecting to it. However, if either half of the molecule 1950 is in selection, i.e., either atoms 1931, 1927, 1929 Or atoms 1931, 1935, 1933 ar ⓡin selection, a valid single ring is recognized.

At step 1825, the array of bonds or ring is normalized by AdjustList. This step re-indexes ring[] so that the bond that is closest to the horizon is first in the array. This makes subsequent identification with standard ring templates more efficient. In the event that two bonds of a ring may be equally close to the horizon (e.g., 30° and 150° bonds of benzene), the bond closest to 185° is chosen. After normalizing, at step 1827 the ringStyle of the ring is found. This indicates how the different bonds are arranged in the ring, for example in benzene: double, single, double, single, double, single. Having reached step 1829, the procedure is certain that the structure is a valid ring, thus, the Boolean variable OptionsShown is set to true.

At step 1831, the ring is identified. First, ringType is set from the ringStyleTable. Here the procedure matches the number of bonds (noBonds) in the ringStyleTable with bondCount, which is set in step 1809. This establishes which ringStyle is used. For example, if bondCount equals six, the noBonds entry in ringStyleTable that matches this indicates that the style is sixMemberRingStyle. At step 1832, the style of ring is matched against the templates stored in the proper RingStyleArray. For the previous example, the style is sixMemberRingStyle, thus, the following templates are searched:

```
sixMemberRingStyle: RingStyleArray = [
 [single, single, single, single, single, single, other, other],
 [single, single, single, single, double, single, other, other],
 [single, single, double, single, double, single, other, other],
 [single, double, single, single, double, single, other, other],
 [double, single, double, single, double, single, other, other],
 NullStyle, NullStyle, NullStyle];
```

If the first ringStyle is matched at step 1833, i.e., ringStyle[0], then all the bonds in the ring are single, and the ring is identified. At step 1835, the procedure return but first checks the interior of the ring for a circle (indicating aromaticity). Such a check is only necessary if all the ring bonds are single. If the ring is not matched by step 1837, then at step 1841, the style of the ring is rotated by one bond. In other words, the index of the ring array is incremented by one. The procedure loops back to step 1832 to retest the ring against the templates.

This process continues until either a match is found or all the possible styles are exhausted. Step 1843 detects this latter case, and sets the variable ringOption to last. This indicates that although there is a ring, it is not identified with known rings. Otherwise, at step 1845 the identified ringStyle is accepted and the procedure returns.

Because of the rapidly increasing number of single/double bond arrangements as a ring's members increase, it becomes increasingly more difficult to give the user efficient access to all possible arrangements for a ring. The invention recognizes this problem and provides a unique solution. Bond "shifting," the rotation of bonds on a ring, solves this problem by limiting the number of choices which must be displayed on the screen. For example, instead of displaying twenty different rings styles for a six-member ring, the system displays only six styles (FIG. 17, 1713, 1715) and two Shift Bond softkeys (FIG. 17, 1717, 1719). Bond shifting is available when the user draws a ring or selects a structure which RingDetection recognizes as a ring.

Figure 20:
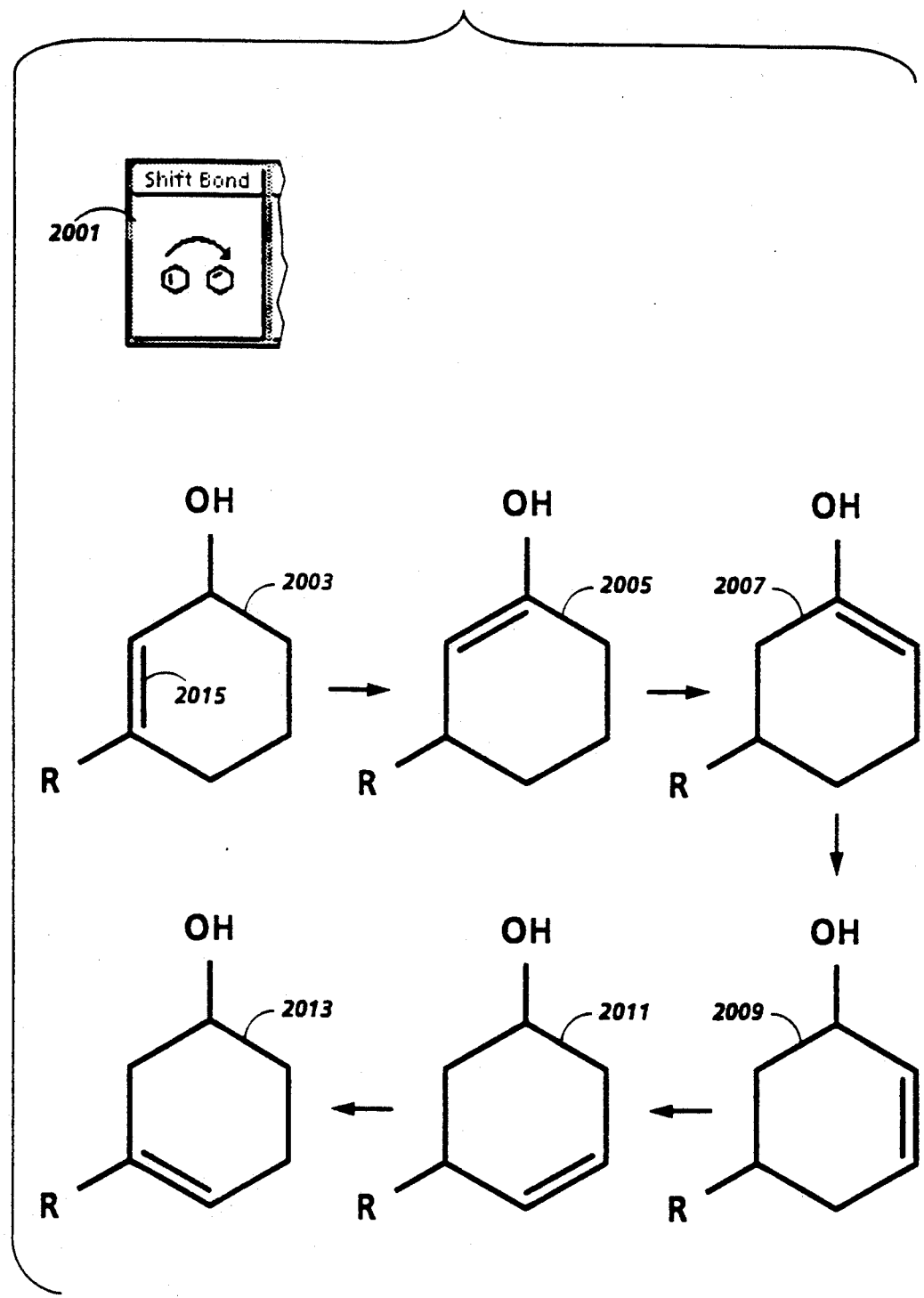
FIG. 20 illustrates the operation and efficiency of shifting bonds.

FIG. 20 illustrates the efficiency gains of bond shifting. For example, to shift a double bond in a hexagonal ring, the user selects the Shift Bond softkey 2001 from the ring softkeys (FIG. 17, 1700). Both clockwise 1717 and counter-clockwise 1719 bond shifting are available. For each mouse click on the Shift Bond softkey 2001, the bond 2015 rotates one position clockwise. The rings 2005, 2007, 2009, 2011, 2013 in FIG. 20 display the six possible arrangements for a double bond 2015 in the hexagonal ring 2003. It should be noted that the ring 2003 remains stationary in bond shifting.

The actual bond shifting is accomplished by re-indexing the array for a ring. Ring 2003 is recognized by RingDetection to be of the following ringStyle:

[single, single, single, single, double, single, other, other].

Its displayed style is:

[single, double, single, single, single, single, other, other].

In other words, the reference bond (the one closest to 185°) is a single bond followed in a clockwise fashion by double, single, single, single, and single bonds. To shift the bond 2015 clockwise by one position, the index of the displayed type array is shifted by one, thus yielding the new array:

[single, single, double, single, single, single, other, other].

and displaying the new structure 2005.

The present invention contemplates other bond shifts as well, for example, shifting the three double bonds in a Kekule structure from:

[double, single, double, single, double, single other, other], to:

[single, double, single, double, single, double, other, other];

or three counter-clockwise shifts of two double bonds in an octagon by re-indexing:

[single, single, single, single, double, single, double, single], into:

[single, double, single, double, single, single, single, single].

While the invention is described in some detail with specific reference to a single preferred embodiment and certain alternatives, there is no intent to limit the invention to that particular embodiment or those specific alternatives. The true scope of the invention is defined not by the foregoing description but by the following claims.

What is claimed is:

1. A computer-aided chemical illustrating method for drawing a bond which comprises the steps of:
   entering a bond drawing mode;
   generating a first mouse signal at a first screen location to define the starting point of said bond;
   generating a second mouse signal, different from said first mouse signal, at a second screen location; and
   displaying a bond beginning at said starting point, said bond having an endpoint at a screen location corresponding to said second screen location.

2. The method of claim 1, further comprising the steps of:
   generating a signal other than said second signal; and
   exiting said bond drawing mode.

3. The method of claim 1, wherein said endpoint is placed at said second screen location.

4. The method of claim 1, wherein said endpoint is placed at a fixed length from said starting point and at a angle relative to said starting point which is one of a set of constraint values.

5. The method of claim 4, wherein said angle is chosen to be the constraint value which is closest to the angle of said second screen location relative to said starting point.

6. The method of claim 1, further including the steps of:
   generating said second signal at a third screen location; and
   displaying a second bond beginning at said endpoint of said bond, said second bond having an endpoint screen location corresponding to said third screen location.

7. A computer-aided chemical illustrating method of changing bond type, comprising the steps of:
   entering a bond drawing mode;
   selecting a plurality of screen control points which specify a bond;
   displaying a plurality of bond types including at least a single bond and a double bond, and softkeys, each of said bond types corresponding to a softkey;
   selecting a double bond type form said plurality of bond types by activating the softkey corresponding to a double bond; and
   displaying said double bond type along said screen control points.

8. The method of claim 7, wherein said displaying a plurality of bond types step comprises displaying softkeys for a plurality of bond types.

9. A computer-aided chemical illustrating method of determining the bisect angle for a plurality of bonds, comprising the steps of:
   selecting an atom;
   determining a plurality of bonds which connect to said atom;
   determining an angle for each said bonds;
   computing a bisect angle from said angle of each said bond;
   computing an extension angle from said bisect angle; and
   constraining a bond drawing angle to match said extension angle or said bisect angle.

10. The method of claim 9, further comprising the steps of:
    declaring an angle array;
    defining a plurality of user angles;

inserting said plurality of user angles into said angle array;

inserting said bisect angle and said extension angle into said angle array; and constraining a bond drawing angle to match said angle array.

11. A computer aided-chemical illustrating method for determining atom label alignment, comprising the steps of:

selecting an atom;
entering a label;
determining a bond which connects to said atom;
determining an angle for said bond;
determining an endpoint for said bond which is not at said atom location;
computing an average location for said endpoint;
comparing said average location to said atom location;
computing an alignment value from said average location and said atom location; and
displaying said label at said atom based on said alignment value.

12. A computer-aided chemical illustrating method of atom labeling, comprising the steps of:

selecting an atom;
defining a label to apply to said atom;
storing the location of said atom;
determining a bond which connects to said atom;
determining an angle for said bond;
determining an endpoint for said bond which is not at said atom location; and
displaying said label at said atom based on said alignment value.

13. The method of claim 12, further comprising the steps of:

displaying direction indicators in an atom label window;
selecting said direction indicator; and
moving said label in response to said direction indicator selecting step.

14. A computer-aided chemical illustrating method of atom label alignment, comprising the steps of:

selecting an atom;
defining a label to apply to said atom;
displaying direction indicators in an atom label window;
selecting said direction indicator; and
moving said label i response to said direction indicator selecting step.

15. A computer-aided chemical illustrating method for displaying rings, comprising the steps of:

displaying a plurality of rings, and softkeys, each of said rings corresponding to a softkey;
selecting a ring from said plurality of rings by activating the softkey corresponding to said ring;
displaying a bond shifting softkey;
selecting said bond shifting softkey; and
determining a display ring from said ring selecting and said bond shifting steps.

16. The method of claim 15, wherein said displaying a plurality of rings step comprises displaying a softkey with a plurality of rings.

17. In a computer system having a processor, a memory, a display device, and an input device, a chemical illustration system comprising:

bond drawing means stored in said memory for drawing different bond types to be drawn and labeled while in a drawing mode;

auto-label alignment means stored in said memory for automatically aligning atoms;

custom label alignment means stored in said memory for custom aligning labels;

orientation means stored in said memory for changing an orientation or a style of an object being drawn while drawing;

ring detection means stored in said memory for detecting which type of ring a user has selected; and bond shifting means stored in said memory for moving bonds around on a chemical ring.

18. A system for bond drawing comprising:

means for entering a bond drawing mode, coupled to;
means for generating a first mouse signal at a first screen location, to define a starting point for said bond, coupled to;
means for generating a second mouse signal, different from said first mouse signal, at a second screen location, coupled to;
means for displaying a bond beginning at said starting point, said bond having an endpoint at a screen location corresponding to said second screen location.

19. The system of claim 18, further comprising:

means for generating a subsequent second signal at a subsequent location; and
means for displaying a bond from said second location to said subsequent location.

20. The system of claim 18, further comprising:

means for generating a signal other than said second signal; and
means for exiting said bond drawing mode.

21. The system of claim 18, wherein said generating means comprises a two button mouse.

22. A system for changing bond type, comprising:

means for entering a bond drawing mode, coupled to;
means for selecting a plurality of control pints which specify a bond, coupled to;
means for displaying a plurality of bond types including at least a single bond and a double bond, and means for displaying a plurality of softkeys, each of said bond types corresponding to a softkey, coupled to;
means for selecting a double bond type from said plurality of bond types by activating the softkey corresponding to a double bond; and
means for displaying said double bond type along said control points.

23. The system of claim 22, wherein said displaying means comprises means for displaying softkeys for a plurality of bond types.

24. A system of determining the bisect angle for a plurality of bonds, comprising:

means for selecting an atom, coupled to;
means for determining a plurality of bonds which connect to said atom, coupled to;
means for determining an angle for each said bonds, coupled to;
means for computing a bisect angle from said angle of each said bond, coupled to;
means for computing an extension angle from said bisect angle; and
means for constraining a bond drawing angle to match said extension angle or said bisect angle.

25. The system of claim 24, further comprising:

means for declaring an angle array, coupled to;
means for defining a plurality of user angles, coupled to;

means for inserting said plurality of user angles into said angle array, coupled to;

means for inserting said bisect angle and said extension angel into said angle array; and means for constraining a bond drawing angle to match said angle array.

26. A system for determining atom label alignment, comprising:

means for selecting an atom; coupled with means for entering a label; coupled with means for determining a bond which connects to said atom; coupled with means for determining an angle for said bond; coupled with means for determining an endpoint for said bond which is not at said atom location; coupled with means for computing an average location for said endpoint; coupled with means for comprising said average location to said atom location; coupled with means for computing an alignment value from said average location and said atom location; and coupled with means for displaying said label at said atom based on said alignment value.

27. A system of atom labeling, comprising:

means for selecting an atom; coupled with means for defining a label to apply to said atom; coupled with means for storing the location of said atom; coupled with means for determining a bond which connects to said atom; coupled with means for determining an angle for said bond; couple with means for determining an endpoint for said bond which is not at said atom location; and coupled with means for displaying said label at said atom based on said alignment value.

28. The system of claim 27, further comprising:

means for displaying direction indicators in an atom label window; coupled with means for selecting said direction indicator; and coupled with means for moving said label in response to said direction indicator selecting step.

29. A system of atom label alignment, comprising:

means for selecting an atom; coupled with means for defining a label to apply to said atom; coupled with means for displaying direction indicator sin an atom label window; coupled with means for selecting said direction indicator; and coupled with means for moving said label in response to said direction indicator selecting step.

30. A system for displaying rings, comprising:

means for displaying a plurality of rings and softkeys, each of said rings corresponding to a softkey; coupled with means for selecting a ring from said plurality of rings by activating the softkey corresponding to said ring; coupled with means for displaying a bond shifting key; coupled with means for selecting said bond shifting key; and coupled with means for determining a display ring from said ring selecting and said bond shifting steps.

31. The system of claim 30, wherein said displaying a plurality of rings step comprises displaying a softkey with a plurality of rings.

32. A computer-aided chemical illustrating method of changing bond type, comprising the steps of:

entering a bond drawing mode;

selecting a plurality of screen control points which specify at least one bond;

displaying a plurality of bond types and softkeys without leaving said drawing mode, each of said bond types corresponding to a softkey;

selecting a bond type form said plurality of bond types by selecting the softkey corresponding to said bond type; and displaying said bond type along said screen control points.

33. A computer-aided chemical illustrating method of atom labelling, which comprises the steps of:

entering a bond drawing mode;

displaying an atom label window without leaving said drawing mode;

selecting an atom;

creating a label in said atom label window; and displaying said label at said atom.

34. The method of claim 33 wherein said atom is selected automatically.

35. A computer-aided chemical illustrating method for changing structure orientation, which comprises the steps of:

entering a drawing mode;

selecting a plurality of screen control points which specify at least one bond;

displaying a plurality of different orientations and softkeys without leaving said drawing mode, each of said orientations corresponding to a softkey;

selecting an orientation from said displayed plurality by activating the softkey corresponding to said orientation; and displaying said selected orientation along said screen control points.

36. The method of claim 35, wherein said plurality of different orientations comprises a plurality of ring orientations.

37. The method of claim 35, wherein said plurality of different orientations comprises a plurality of chain orientations.

38. A computer-aided chemical illustrating method for changing structure type, which comprises the steps of;

entering a drawing mode;

selecting a plurality screen control points which specify at least one bond;

displaying a plurality of different structure types and softkeys without leaving said drawing mode, each of said structure types corresponding to a softkey;

selecting a structure type form said displayed plurality of different structure types by activating the softkey corresponding to said structure type; and displaying said selected type along said screen control points.

39. The method of claim 38, wherein said plurality of different types comprises a plurality of ring types.

40. The method of claim 38, wherein said plurality of different types comprises a plurality of chain types.

41. A computer-aided chemical illustrating method for changing structure style, which comprises the steps of:

entering a drawing mode;

selecting a plurality of screen control points which specify at least one bond;

displaying a plurality of different styles and softkeys without leaving said drawing mode, each of said styles corresponding to a softkey;

selecting a style from said displayed plurality of different styles by activating the softkey corresponding to said style; and displaying said selected style along said screen control points.

42. The method of claim 41, wherein said plurality of different styles comprises a plurality of ring styles.

43. The method of claim 41, wherein said plurality of different styles comprises a plurality of chain styles.

44. An appropriately configured digital computer system programmed for implementing the method of claim 32, or claim 33, or claim 35, or claim 38, or claim 41.

* * * * *

UNITED STATES PATENT AND TRADEMARK OFFICE
CERTIFICATE OF CORRECTION

PATENT NO. : 5,249,137

DATED : September 28, 1993

INVENTOR(S) : James S. Wilson, et al.

It is certified that error appears in the above-identified patent and that said Letters Patent is hereby corrected as shown below:

Delete claims 7, 8, 15, 16, 22, 23, 30-32, and 35-44.

Signed and Sealed this

Fifth Day of September, 1995

Attest:

BRUCE LEHMAN

Attesting Officer      *Commissioner of Patents and Trademarks*